(12) United States Patent
Akgul et al.

(10) Patent No.: US 7,162,073 B1
(45) Date of Patent: Jan. 9, 2007

(54) METHODS AND APPARATUSES FOR DETECTING CLASSIFYING AND MEASURING SPOT DEFECTS IN AN IMAGE OF AN OBJECT

(75) Inventors: Yusuf Akgul, Northboro, MA (US); Ivan Bachelder, Newton, MA (US); Adam Wagman, Framingham, MA (US); Jason Davis, Bellingham, MA (US); Juha Koljonen, Needham, MA (US); Prabhav Morje, Natick, MA (US)

(73) Assignee: Cognex Technology and Investment Corporation, Mountain View, CA (US)

(*) Notice: Subject to any disclaimer, the term of this patent is extended or adjusted under 35 U.S.C. 154(b) by 509 days.

(21) Appl. No.: 10/001,177

(22) Filed: Nov. 30, 2001

(51) Int. Cl.
G06K 9/00 (2006.01)
G01N 21/00 (2006.01)

(52) U.S. Cl. .................. 382/149; 382/199; 382/224; 382/262; 348/92; 348/125; 356/73.1; 356/239.2

(58) Field of Classification Search ........ 382/141–152, 382/190, 199, 204, 212, 213; 356/73.1, 237.1, 356/239.2
See application file for complete search history.

(56) References Cited

U.S. PATENT DOCUMENTS

| | | |
|---|---|---|
| 5,179,419 A | 1/1993 | Palmquist et al. |
| 5,319,734 A | 6/1994 | Buzzetti |
| 5,535,002 A | 7/1996 | Csipkes et al. |
| 5,543,915 A | 8/1996 | Csipkes et al. |
| 5,596,672 A | 1/1997 | Harman et al. |
| 5,600,439 A | 2/1997 | Csipkes et al. |
| 5,636,020 A | 6/1997 | Csipkes et al. |
| 5,657,131 A | 8/1997 | Csipkes et al. |
| 5,671,049 A | 9/1997 | Csipkes et al. |
| 5,727,327 A | 3/1998 | Wakabayashi et al. |
| 5,729,622 A | 3/1998 | Csipkes et al. |
| 5,729,966 A | 3/1998 | Grulick |
| 5,768,401 A | 6/1998 | Csipkes et al. |
| 5,768,409 A | 6/1998 | Csipkes et al. |
| 5,809,162 A | 9/1998 | Csipkes et al. |
| 5,857,047 A | 1/1999 | Strand et al. |
| 5,857,049 A | 1/1999 | Beranek et al. |
| 5,862,250 A | 1/1999 | Csipkes et al. |
| 5,898,494 A | 4/1999 | Csipkes et al. |
| 5,923,781 A | 7/1999 | Csipkes et al. |
| 5,926,568 A * | 7/1999 | Chaney et al. .............. 382/217 |

(Continued)

OTHER PUBLICATIONS

Evan Lubofsky, Machine vision takes guesswork out of fiber-polishing inspection, Laser Focus World, Sep. 2001.

Primary Examiner—Jingge Wu
Assistant Examiner—Charles Kim
(74) Attorney, Agent, or Firm—Russ Weinzimmer

(57) ABSTRACT

A method is provided for detecting spot defects on an object when an allowable variation (called the "background") in the appearance of the object can be modeled. Methods are also provided for measuring and classifying detected spot defects. An alignment model is used to align the image of the object, a background model is then used to estimate the (possibly different) background in each region, and each background is substantially removed from the image so as to form a foreground image on which blob analysis can be applied to detect spot defects, the blob analysis using a threshold image that accommodates different noise statistics for each region. The method facilitates robust spot defect inspection of fiber optic end faces, or of any object with different object regions. The method also allows use of blob analysis over a larger range of conditions, including conditions that make simple blob analysis infeasible.

21 Claims, 10 Drawing Sheets

U.S. PATENT DOCUMENTS

| | | |
|---|---|---|
| 5,995,212 A | 11/1999 | Dar et al. |
| 6,002,793 A * | 12/1999 | Silver et al. ................. 382/152 |
| 6,061,476 A * | 5/2000 | Nichani ....................... 382/270 |
| 6,067,374 A * | 5/2000 | Fan et al. .................... 382/135 |
| 6,069,991 A | 5/2000 | Hibbs-Brenner et al. |
| 6,088,498 A | 7/2000 | Hibbs-Brenner et al. |
| 6,105,396 A | 8/2000 | Glodis et al. |
| 6,167,150 A * | 12/2000 | Michael et al. ............. 382/149 |
| 6,183,343 B1 | 2/2001 | Buzzetti |
| 6,298,149 B1 * | 10/2001 | Nichani et al. ............. 382/149 |

* cited by examiner

METHODS AND APPARATUSES FOR DETECTING CLASSIFYING AND MEASURING SPOT DEFECTS IN AN IMAGE OF AN OBJECT

FIELD OF THE INVENTION

This invention relates generally to machine vision, and particularly to defect detection and analysis.

BACKGROUND OF THE INVENTION

It is often a goal of machine vision to detect and precisely measure and/or classify the defects of an object. Such defects might include unexpected and/or undesirable deviations from an ideal or expected object model along boundaries of the actual object, or unexpected and/or undesirable blemishes within the regions between actual object boundaries.

In particular, there is the problem of "spot" defect detection and classification and/or measurement when the shape of the object is known. "Spots" are defined as relatively local regions with grayscale intensity, or possibly texture, that is significantly different from the perceived background of an object. For example, in the context of inspecting a polished end of an optical fiber, spots include pits, chips, contamination, and blemishes. Spots do not include defects that have no consistent difference from the perceived background of the object (such as some faint scratches on polished fiber end faces), nor do they include gradual shading variations. Spots may have any shape.

The most-utilized known method for detecting spot defects is to apply thresholding and morphological processing techniques followed by connected component analysis, which taken together is also called "blob analysis". However, this method assumes that the image of the object can be segmented into foreground (defects) and background (object) with a single threshold, or more generally by a single global mapping. This type of segmentation is not effective when there are different regions within an object to inspect, each region having its own background intensity, and when the background intensity within each of the regions of the object varies (albeit smoothly) in such a way as to make a global intensity segmentation (such as a constant global threshold) determination impossible.

An improvement over the basic blob technique is to use Golden Template Comparison (GTC), in which an ideal grayscale template of the object is first aligned to the image, and then subtracted from the image to produce a foreground image. Blob analysis is then performed on the foreground image. However, GTC still fails if the runtime image of the object is allowed to have certain variations (such as lighting gradients). Also, GTC assumes that a single mapping can segment defects from object in the foreground image.

An alternative to GTC is pre-processing the image with linear filters (e.g., lowpass or bandpass filters) before performing blob analysis, but linear filters often degrade the image near boundaries of the object (causing false defects) and change the appearance of the defects, or even remove the defects. It is also very difficult to impose restrictions about the inspected object's known features in the defect detection with linear filters because they are not easily customizable.

Another approach is to apply an edge-based inspection tool, such as PatInspect®, a product of Cognex Corp. of Natick, Mass., which can detect both boundary deviations and deviations from "blankness" between the boundaries for certain classes of images. Unfortunately, edge-based tools often miss defects with low-contrast boundaries, and also return defects as edge chains that must somehow be connected together to form closed spots. Further, it is very difficult to solve the problem of connecting edge chains to form closed spots.

SUMMARY OF THE INVENTION

The invention provides a general method for detecting spot defects on an object when an allowable (non-defective) variation in the appearance of the object in an image can be modeled and removed. Methods are also provided for measuring and classifying detected spot defects. The allowable variation is also referred to as the "background," and the form of the background may be different in different regions of an image of the object. In accordance with the principles of the present invention, an alignment model is used to align the image of the object, a background model is then used to estimate the background in each region, and the background is substantially removed from the image so as to form a foreground image on which blob analysis can be applied to produce defects. The invention also provides a method for determining a threshold image to be used in the blob analysis that accommodates different noise statistics or other variation for each region, and that can ignore minor variations that are very close to the boundaries. The invention also provides classification of candidate defects as spot defects, non-defects, and optionally as other classes of defects.

In a particular embodiment, the invention detects spot defects in a polished end-face of a fiber-optic cable.

In a preferred embodiment, alignment uses a rotation- and scale-invariant search (RSIS) tool, such as can be found among many geometric pattern matching tools commonly available; in a further preferred embodiment, alignment uses the RSIS tool known as PatMax®, developed and sold by Cognex Corporation, One Vision Drive, Natick, Mass. For fiber end-face inspection, in a further preferred embodiment, alignment performs a deformable alignment which incorporates both PatMax® and a custom core-alignment algorithm that is detailed herein.

In one embodiment, the background regions are specified by labeling each pixel in the model with a region index, and this labeled model is transformed by the runtime alignment pose. In a preferred embodiment, the background regions are specified using geometric shapes, and an implicit or explicit hierarchy, so that each runtime pixel belongs to one region. In another embodiment, runtime pixels may each belong to no regions, one region, or more than one region.

In one embodiment, low-pass filters are used to estimate the background within each region. In a preferred embodiment, median filters are used to estimate the background within each region. For fiber end-face inspection, annular median filters are preferred.

In another general aspect of the invention, a method for detecting spot defects in an image of an object is provided that includes the acts of aligning within the image at least one object region so as to provide at least one aligned object region; estimating, using the image, a background image within the at least one aligned object region; removing the background image from the image within the at least one aligned object region so as to provide a foreground image having at least one foreground region; computing a threshold image for at least one of the foreground regions in the foreground image; removing the threshold image from the foreground image within at least one of the foreground regions so as to provide a defect image; and using connected component analysis to form defects in the defect image. It is sometimes also useful to then classify candidate defects as non-defects, or one of a plurality of possible defect types. It is also sometimes useful to measure at least one metric for each defect.

In a preferred embodiment, the act of aligning performs deformable alignment, which can use core alignment.

The object can be any object, but the invention is especially useful when applied to the inspection of a fiber-optic end face.

In another preferred embodiment, aligning is performed using a rotation-invariant and scale-invariant alignment method.

In another preferred embodiment, estimating includes using a median filter, which can sometimes be an annular median filter.

In another preferred embodiment, using a median filter includes using a median filter of a larger spatial scale to provide a mask for use with a median filter of a smaller spatial scale. Sometimes, the median filter of the larger spatial scale is thresholded to provide the mask.

In yet another preferred embodiment, estimating the background image within the at least one aligned object region includes iteratively fitting a smooth surface to the image within the at least one aligned object region. The smooth surface can be a polynomial curve. Also, outliers can be removed after each iterative fitting.

In some preferred embodiments, removing the background image from the image within the at least one aligned object region so as to provide a foreground image having at least one foreground region includes subtracting the background image from the image.

In other preferred embodiments, computing a threshold image for at least one of the foreground regions in the foreground image includes removing from the at least one of the foreground regions all pixels with a gray level above a threshold.

In some preferred embodiments, computing a threshold image for at least one of the foreground regions in the foreground image includes using histogram analysis.

In other preferred embodiments, computing a threshold image for at least one of the foreground regions in the foreground image includes removing, from the at least one of the foreground regions in the foreground image, pixels with a gray level between two prominent peaks of a multi-modal distribution.

In yet other preferred embodiments, computing a threshold image for at least one of the foreground regions in the foreground image includes adding the gradient of the background image to the threshold image.

In a preferred embodiment, removing the threshold image from the foreground image within at least one of the foreground regions so as to provide a defect image includes subtracting the threshold image from the foreground image within at least one of the foreground regions so as to provide a defect image.

In another preferred embodiment, measuring sub-pixel boundaries of blobs in the foreground image includes edge detection along the boundaries of blobs. Measuring sub-pixel boundaries of blobs in the foreground image can include tracking along the boundaries of blobs. Measuring sub-pixel boundaries of blobs in the foreground image can include performing sub-pixel interpolation along the boundaries of blobs.

In another general aspect of the invention, a method is provided for detecting and measuring spot defects in an image of an object that includes the acts of: generating a foreground image from the image using calibration information, region information, a background mask, and pose information; generating a threshold image from the image using calibration information, region information, the foreground image, a threshold mask, and pose information; and performing connectivity analysis using the foreground image and the threshold image so as to provide zero or more candidate defects.

In a preferred embodiment, at least one candidate defect representing a detected and measured spot defect is verified so as to provide a verified spot defect.

In another preferred embodiment, the detected and measured spot defect is verified by classifying the spot.

In a further preferred embodiment, performing connectivity analysis using the foreground image and the threshold image also provides a mask for use in defect detection.

In a preferred embodiment, the image mask used in generating a foreground image is provided by providing an image of a fiber end face; detecting fretting in the image to provide a fretting image; generating a fretting mask using the fretting image; detecting large defects in the image to provide a large-defect image; generating a large-defect mask using the large-defect image; detecting scratches in the image to provide a scratch image; generating a scratch mask using the scratch image; and combining the large-defect mask, the scratch mask, and the fretting mask so as to provide the background mask.

In yet another preferred embodiment, generating a foreground image includes: estimating the background of the image to provide a estimated background image using region information; subtracting the estimated background image from the image so as to provide a foreground image.

In a further preferred embodiment, generating a threshold image includes: performing gradient analysis on the background image to provide a background threshold image; performing auto-thresholding on the foreground image to provide a foreground threshold image; providing a scratch threshold image; and combining the background threshold image, the foreground threshold image, and the scratch threshold image to provide the threshold image. Auto-thresholding can preferably include histogram analysis and morphology.

In another general aspect of the invention, a method is provided for detecting spot defects in an image of a fiber end face that includes the acts of aligning within the image at least one end face region so as to provide at least one aligned end face region; estimating, using the image, a background image within the at least one aligned end face region using a non-linear filter; subtracting the background image from the image within the at least one aligned end face region so as to provide a foreground image having at least one foreground region; computing a threshold image for at least one of the foreground regions in the foreground image; subtracting the threshold image from the foreground image within at least one of the foreground regions so as to provide a defect image; and using connected component analysis to form defects in the defect image.

In a preferred embodiment, the act of classifying candidate defects as one of non-defects, and one of a plurality of possible defect types is also included.

In a further preferred embodiment, the method also includes measuring at least one metric for each defect.

In a yet further preferred embodiment, aligning is performed using deformable alignment. Deformable alignment can use core alignment.

The invention allows known blob processing techniques to be used on images wherein defects cannot be extracted using a single global threshold or even using an arbitrary global mapping.

The invention allows users to use blob analysis over a larger range of conditions, including conditions that make simple blob analysis infeasible. These conditions include a highly varying image structure which should not be detected as defects, existence of known features that are very similar to defects but are not defects, existence of high amounts of image noise, and constraints on the edge contrast properties of the blobs. Although the invention introduces complex methods for a wide range of challenging conditions, it can also be employed to improve the accuracy and reliability of results even when simple threshold techniques, in conjunction with linear pre-processing, is feasible. For example, in cases where a constant thresholding is feasible, this invention can be used to eliminate blobs that do not show desired edge contrast properties.

BRIEF DESCRIPTION OF THE DRAWINGS

The above and further advantages of the invention may be better understood from the following detailed description, in conjunction with the following figures, wherein.

DETAILED DESCRIPTION

Figure 1:
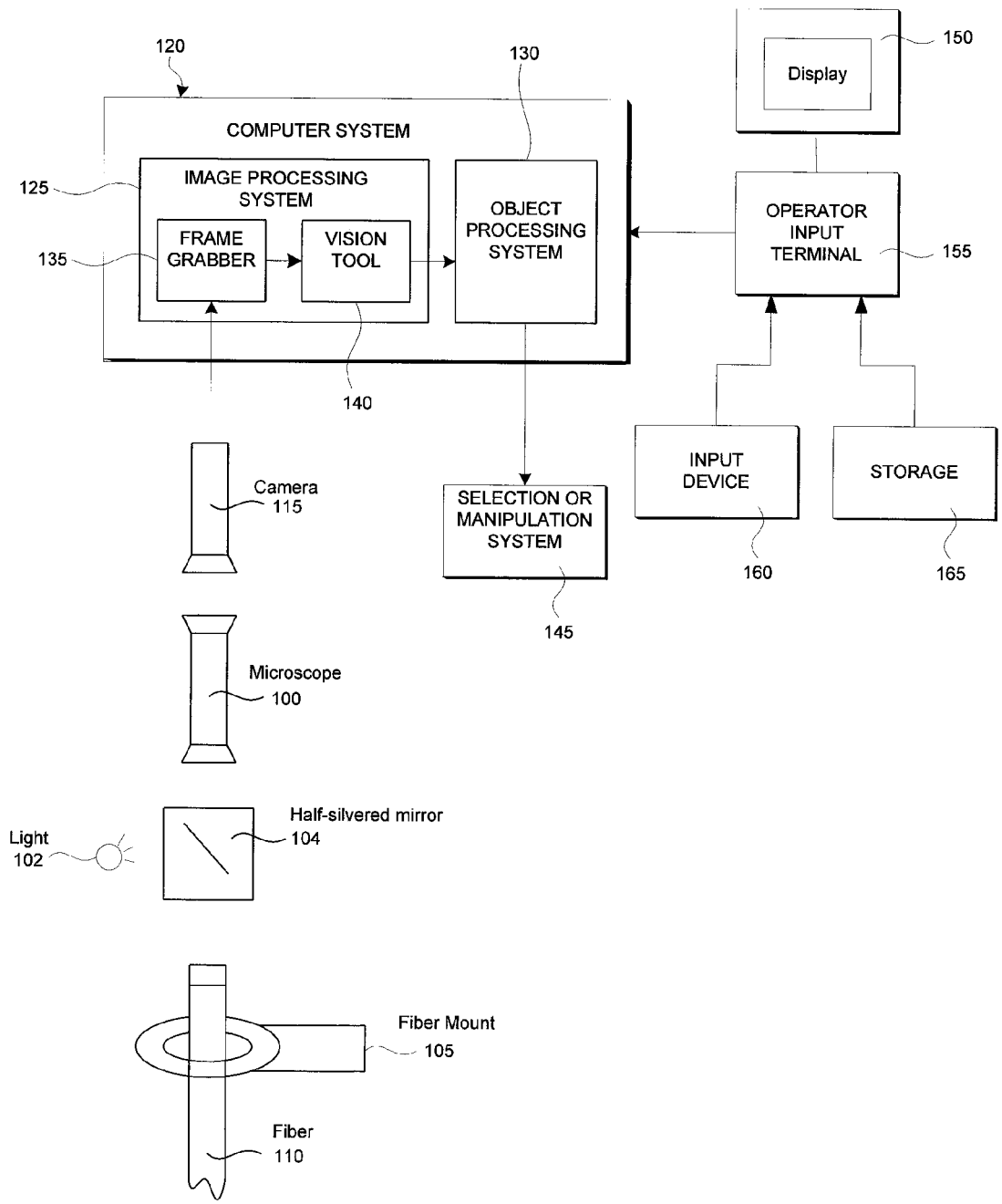
FIG. 1 is a schematic block diagram of a conventional machine vision system.

FIG. 1 illustrates in schematic form an example of a machine vision system that can utilize the process of the present invention. The example system demonstrates the inspection of the end-face of an optical fiber, but this example is merely illustrative and not restrictive. In the example system, a fiber microscope 100 examines an optical fiber 110 held in a mounting device 105. The fiber may also be presented to the system by other well-known mechanisms. When a fiber is in the mount, an image stream of the fiber is created by a camera system 115 in a conventional manner. Light is provided by a light source 102, and a half-silvered mirror 104 is used to direct the light onto the fiber end-face while also allowing the fiber end-face to be imaged by the camera 115. Other arrangements of optics and lighting are possible. The image stream created by the camera 115 is provided to a computer system 120 which processes the image according to the method of the present invention.

The computer system 120 in general comprises an image processing system 125 and an object processing system 130. The image processing system, in turn, includes a frame grabber 135 that creates a series of fixed images from the image stream generated by camera 115. The series of fixed images are provided to a vision tool 140 that detects and measures spot defects in the images in accordance with the principles of the present invention. The vision tool may also detect other types of defects or make additional measurements. The results of the vision tool are then passed to the object processing system 130, which controls a selection or manipulation system 145. The selection or manipulation system treats each fiber 110 based on the results of the object processing 130. For example, if the vision tool finds no critical defects in the fiber, then the object processing system may direct the manipulation system to transfer the fiber to a bin of acceptable fibers, but if the vision tool finds a critical defect, then the object processing system might direct the manipulation system to send the fiber off to be polished again, followed by reinspection. The manipulation system might consist of just a human operator or might be automated. Many other actions are also possible, especially when the present invention is used for applications other than fiber end-face inspection.

In preparation for processing, an operator first "trains" the system to establish a model via the operator input terminal 155. The model contains information necessary for alignment of an image of the object as well as information about the various regions of the object and the type of background that may exist in each region. Since these types of information are conceptually distinct, we will refer to the model as comprising an alignment model and a background model as needed for clarity, although in some implementations the alignment model alone might suffice, such as when the alignment model is specified using geometric shapes and each shape is assumed to be a distinct region and the type of background variation is known already or can be determined from the shapes and/or training image, if any.

The training of the model may be performed in several manners. For example, an image containing an object to be inspected may be presented to the operator on a display 150 associated with operator input terminal 155. The operator can then select an object of interest by "drawing" a box around the object using an input device 160 or by other suitable means. Once the object has been selected, the computer system 120 may use the object image to generate the model. Additionally or alternatively, information for training may be loaded from storage device 165, including but not limited to the possibility of such information being the stored result of a previous interactive training. For example, in an embodiment that used normalized correlation for alignment, the selected image might simply be used as the correlation template. Alternatively, in a preferred embodiment, geometric pattern matching is used for alignment, and a geometric description of the object is already known to the system, so that training finds the best translation, scale, rotation, and possibly other (even nonlinear) degrees of freedom, as is known in the art, to match the geometric description to the training image. For example, in fiber end-face inspection, the geometric description might simply be a circle, and training would locate the circle that represented the fiber cladding and measure its diameter. The description might also include stress rods, as shown in FIG. 4. It may also be possible in some applications to automatically generate a geometric description from an image given only a few constraints, as can be accomplished using the Geometric Description Editor produced by Cognex Corp.

Training must also produce the background model, which consists of a region specification of the set of distinct background regions and the type of expected background variation in each. The region specification might be a set of geometric boundaries in the image plane, or it might be a set of region indices, at least one for each pixel of the model; other representations of the region specification are within the scope of the invention. Note that the region specification may be more or less complex than the alignment model, since there may be features used for alignment that do not require separate background estimation and there may be regions where separate background estimation is required that are not suitable for alignment. Also note that it is possible for some regions of the model to be of no interest to the user. The pixels of such a region are said to be in an ignored region of the model, although some implementations might treat such pixels as though they belonged to no region, i.e. such ignored regions may not be explicitly represented. For simplicity, we will usually say that every pixel of the model and of the runtime image belongs to at least one region, although some of those regions may be ignored (either processed and the results left unexamined, or left completely unprocessed). Regions need not be bounded. For example, in fiber end-face inspection, the fiber cladding is typically represented by a circle, and one region (corresponding to the fiber cladding) is inside the circle and another region (corresponding to the ferrule) is the outside of the circle, which is an unbounded region. At runtime, the outside region is considered to be the entire image outside of the circle.

Note that any expected substantial intensity boundary in the object typically needs to be a region boundary in the region specification, unless the background estimation technique specifically models such an intensity boundary. Otherwise, background estimation would include information from both sides of the intensity boundary and would thus be substantially incorrect. For example, consider an object which is expected to appear as a mostly bright square with a mostly dark circular hole, and suppose for simplicity that a large square median filter were used as the background estimator. Clearly, if the square and hole were treated as a single region, then the background would be substantially wrong near the hole boundary. The regions may be determined automatically using the Geometric Description Editor or similar technique, or it may be specified independently by the operator, either using input device 160 to draw the various geometric regions or using a pre-generated synthetic description, possibly fit to a training image as was done for the alignment model. In a preferred embodiment, the alignment model and background model both use the same geometric description after fitting to a training image. In some applications, the descriptions may be similar but not identical, such as when some background region is not useful for alignment (perhaps because of an indistinct border or a highly unreliable appearance), or when some alignment boundary does not represent a distinct background region.

Typically, each pixel in an image of an object should be assigned to exactly one background region, although it is possible for a pixel to be assigned to multiple regions without departing from the scope of the present invention. (As mentioned previously, one may also think of some pixels as belonging to no region if the region to which they would belong is not of interest.) As is known to those skilled in the art, it is typically necessary to know or to determine a hierarchy for the regions from the shapes in order to assign each pixel to a single region. For example, if the regions were specified using two concentric circles, then there would be one region comprising the pixels within the inner circle, one region comprising the pixels within the outer circle but not within the inner circle, and one region outside the outer circle; of course, one could specify that one or more of those regions was of no interest, e.g. the region outside the outer circle. In fiber end-face inspection, the regions usually consist of the fiber core, the fiber cladding (excluding the core and any stress rods), optionally any stress rods, and the ferrule (the region outside the cladding). For example, the ferrule often appears bright and the fiber cladding often appears dark, so that it is necessary to estimate the background separately in the two regions; treating the ferrule and fiber cladding as a single region would usually cause the estimated background to be substantially incorrect near the border between the two.

Training also needs to specify the type of background variation within each region; the "background" is the expected structure in a defect-free image. Typically, the background consists of a large-scale (i.e. low-frequency) intensity variation within a given region, such as the variation caused by a lighting gradient. For such a background, a low-pass filter is a good estimator of the background. In a preferred embodiment, the filter shape is chosen to match the expected gradient shape. For example, in fiber end-face inspection, there is often a primarily radial gradient (i.e. the background intensity is approximately a function of the distance from the fiber center), and an annular median filter, as described later, is a very good background estimator. It is also possible for the background to consist of a certain texture, and in such cases other filtering techniques (such as bandpass filtering in the frequency domain or texture segmentation) could be used to estimate the background, as is known to those skilled in the art. The background could also consist of an expected image, possibly modified by one of the aforementioned or other types of variation.

Training may attempt to discover the type of background variation within each region, given the background region description and the assumption that the training image is defect-free. For example, if it is known that the expected lighting gradient is linear along an unknown direction, then training might try varying the direction until the best match to the observed variation was found, and then use that direction for background estimation at runtime. In a preferred embodiment, the type of background variation is known ahead of time and fixed. For example, in fiber end-face inspection, the cladding background is assumed to consist of a radial intensity variation which is approximately concentric with the fiber; the core background may have the same center or a slightly different one, as determined by the alignment procedure.

Figure 2:
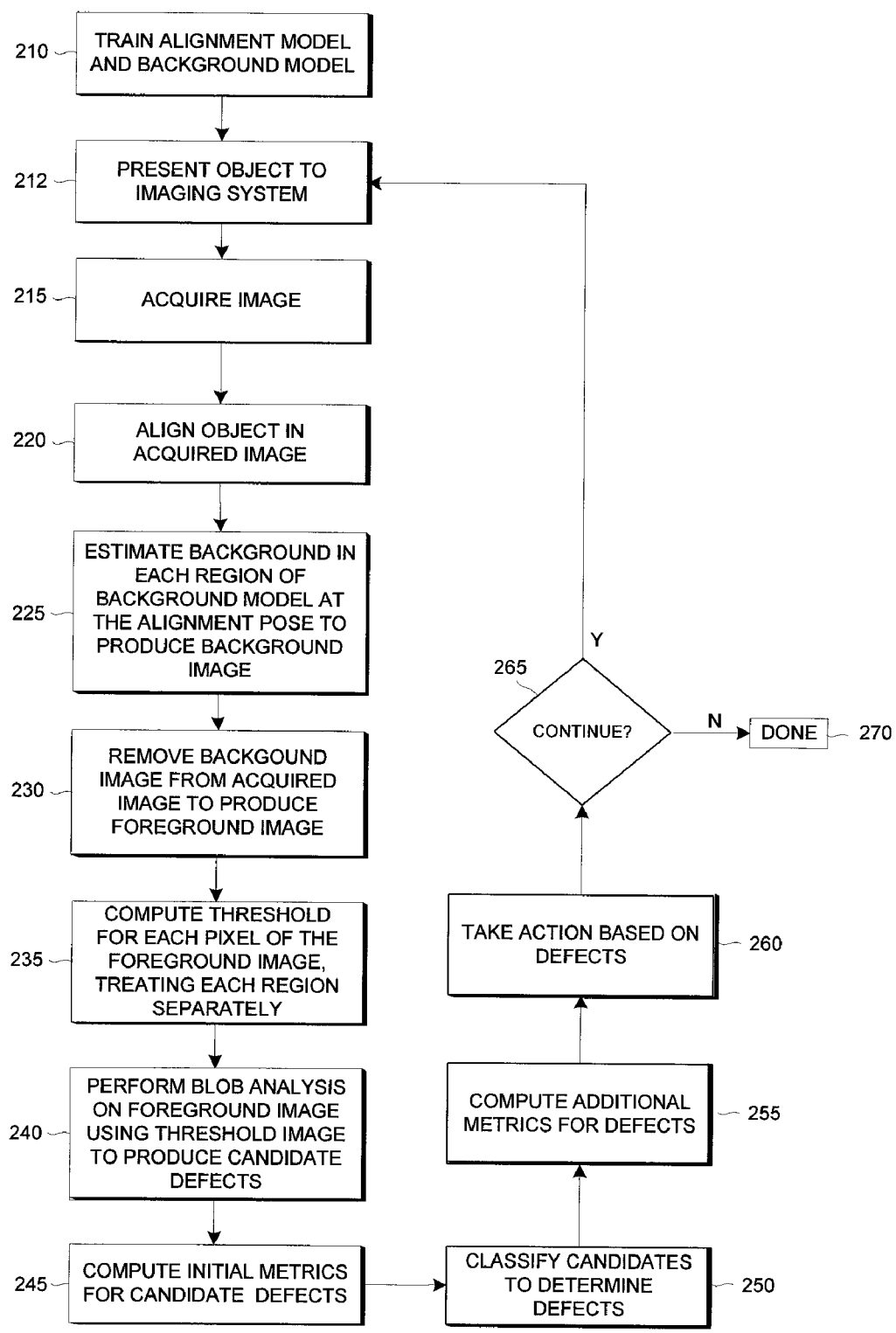
FIG. 2 is a top-level flowchart of the invention.

Steps in the method for detecting spot defects in an image of an object are shown in FIG. 2. The process begins in step 210, where a model of the object is created. In step 212, an object is presented to the camera 115, such as by placing a fiber in the mounting device. In step 215, an image of the object is acquired as discussed above. Then, in step 220, the acquired image is searched using the alignment model to determine the pose (e.g. translation, rotation, and scale, but also including nonlinear transformations) of each region of the object in the image. Note that alignment may be flexible, i.e. the various regions may have different poses. For example, a fiber end-face may typically be represented by a circle for the cladding, a circle for the fiber core, and zero or more elements representing stress rods (usually spaced on the circumference of a hypothetical third circle), and although the cladding circle, core circle, and the stress rod circle are usually approximately concentric, they are not strictly so. Thus alignment may determine the poses for each of the elements separately or in conjunction. It is often convenient to speak of the alignment pose for the object as a whole, and it should be understood that such a pose may include flexible distortions amongst the various regions of the object. Once the alignment pose has been determined, the background is estimated using the background model in step 225. The background image is then subtracted or otherwise removed from the acquired image to form the foreground image in step 230.

Next, in step 235, a defect threshold for each background region is computed from the background and foreground images. For a background which consists of a grayscale intensity variation and a foreground image computed by subtracting the background image from the acquired image, the defect threshold is the value above which a pixel in the foreground image is considered a defect pixel. Note that later processing may decide that the pixel does not belong to an actual defect, e.g. a connected set of defect pixels may be discarded by later classification. In general, the defect threshold is a set of quantities that can be used to segment the foreground image into defect pixels and non-defect pixels.

In step 240, connected component analysis, also referred to as blob analysis, is performed to connect defect pixels into defects. It is also possible to perform a modified version of such an analysis to split one connected defect into multiple defects or to merge nearby connected defects into a single defect, as may be appropriate for various applications and as known to those skilled in the art.

In some applications, further processing of defects may be done to compute various metrics and/or to classify defects. Such classification also includes the possibility of deciding that a connected "defect" is not actually a defect, or at least not a defect of interest. For example, in fiber end-face inspection, defects which are narrow and highly elongated are typically ignored, since they usually represent scratches, which can be detected by an entirely different technique. When such classification may be performed, it may sometimes be convenient to refer to the defects produced by connected component analysis (either before or after any splitting or merging) as candidate defects, and to reserve the term "defect" for those candidate defects which are classified as being of interest. It is also sometimes convenient to refer to some classified defects as "spot defects," particularly when some of the classified defects may represent real defects in the object but not a defect that should be reported. Again, this is useful when, for example, speaking of spots and scratches in fiber end-face inspection, since the present invention may detect both spots (e.g. pits and chips) and polishing scratches, but the user may desire only the spots to be reported, typically because the scratches will be detected by a separate technique.

In step 245, a set of metrics is computed for each candidate defect. Next, in step 250, the candidate defects are classified as defects or non-defects; they may optionally be classified into distinct types of defects. If there is only one class of defects, classification may also be referred to as filtering or verification. In step 255, some additional metrics may be computed for the final defects; these metrics may have been omitted from step 245 because they are computationally intensive and not necessary for the classification 250 or because some metrics should be computed only for certain classes of defect.

In step 260, the classification and metric results from the previous steps are passed to the object processing system 130, which takes action based on the results. For example, in fiber end-face inspection, if the fiber is considered to have defects that would interfere with the transmission of the signal (especially defects near the fiber core), then the fiber might be returned for additional polishing and then re-inspected. If the fiber does not have such defects, the fiber might be passed on to a final packaging station.

In step 265, a determination is made whether to continue processing additional images. If the decision is to continue, processing returns to step 212, where a new object (or the same object, presumably after some modification) is presented to the system. Otherwise, processing stops with step 270.

Figure 3:
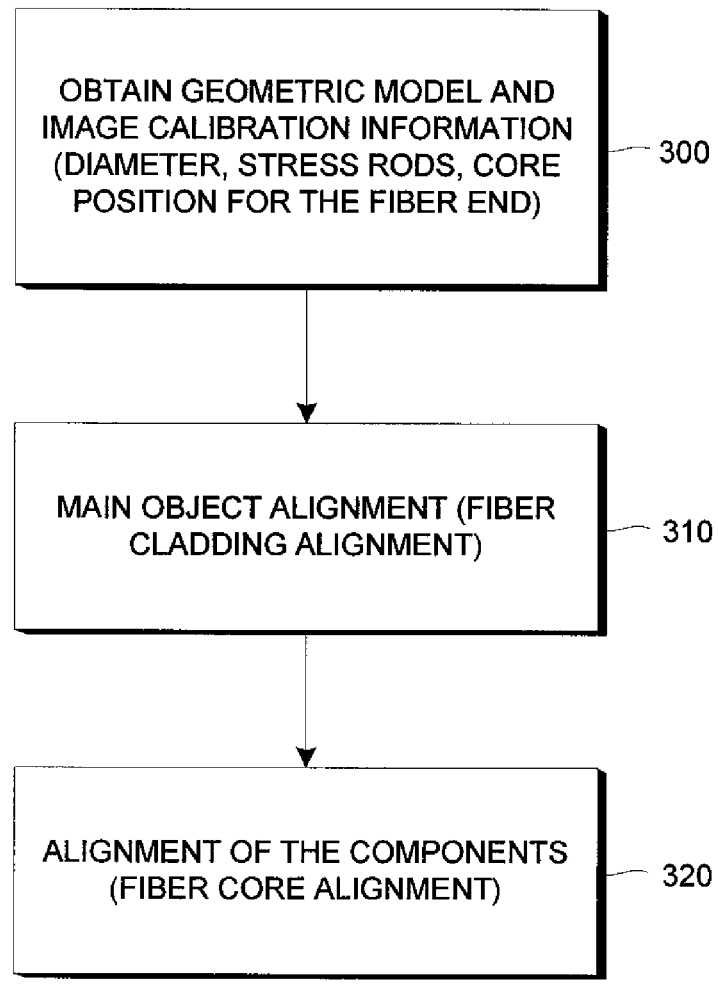
FIG. 3 is a flowchart illustrating steps for object alignment.

The alignment performed in step 220 is detailed in FIG. 3. In general, regions of the inspected object might be aligned using a number of alternative techniques depending on the application. For example, normalized correlation search, including one that uses templates at a variety of rotations and scales, may be used. Alternatively, a geometric feature-matching search tool capable of aligning several degrees of freedom, such as translation, rotation, and scale, may be used. A further possibility for the alignment is to employ the Generalized Hough Transform, including extensions of which that are scale-invariant and orientation-invariant, as is known in the art. The use of any alignment technique is within the scope of the present invention. For any of these techniques, alignment may be performed using features of the entire object, or using only features from a portion of the object. Alignment may even be performed using the features of another object that has a known spatial relationship to the object that is to be inspected for spots (a method commonly referred to as "fixturing"). In a preferred embodiment, the geometric feature-matching tool PatMax®, a product of Cognex Corp., is used for alignment.

In one preferred embodiment, separate regions or components of the object are aligned separately in order to tolerate variations of the component positions from one instance of the object to the next. Moreover, the optimal alignment methods that might be used to separately align each region or component typically differ due to differing imaging conditions or object characteristics. For example, in the case of fiber end-face inspection, the cladding, core, and stress rods components of the fiber end are separately aligned using several different alignment techniques. In a preferred embodiment, in step 300, the alignment accepts the geometric model for the fiber end face and the image calibration information that relates the image pixels to the real world units. The calibration information can be a linear mapping between the image pixels and the real world units that includes rotation, scaling, shear, and aspect ratio relations. The calibration can also be a nonlinear mapping due to distortions during the formation of the object image as a result of perspective projection distortions, optics distortions, etc. The calibration can be obtained using a number of methods including using calibration plates in front of the system camera, or any other popular technique known to the skilled in the art.

Figure 4A:
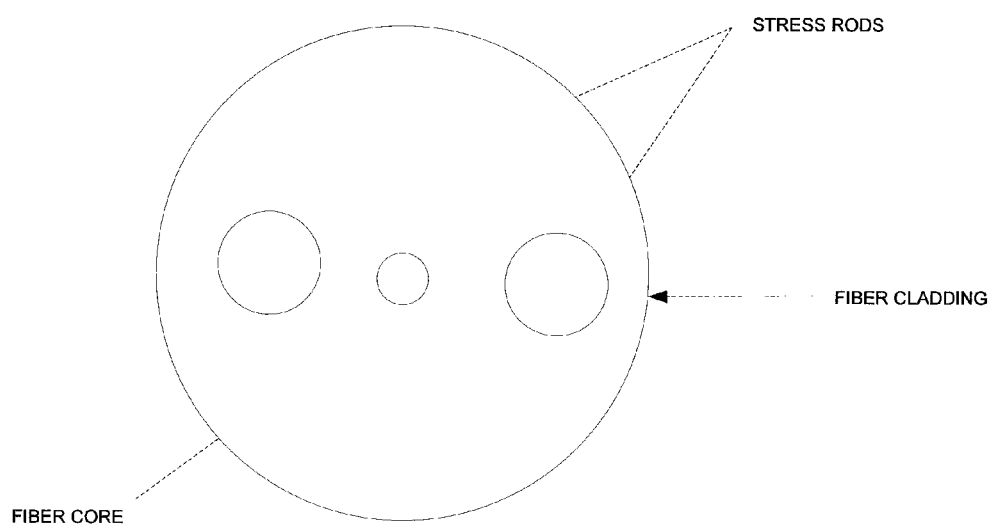
FIG. 4 is a diagram illustrating a geometric model of a fiber end face and its use in alignment.

In the same embodiment, in step 310 the fiber cladding is first aligned and in step 320 the resulting alignment pose for the cladding is used to constrain the alignment of the fiber core, if present, and the stress rods, if present. Alignment models for each of these regions are constructed using a geometric description of the fiber, which is supplied by the operator. FIG. 4A illustrates a geometric model of a typical fiber end face that includes visible stress rods and fiber core.

Figure 4B:
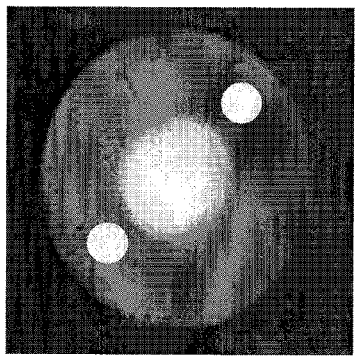
Figure 4C:
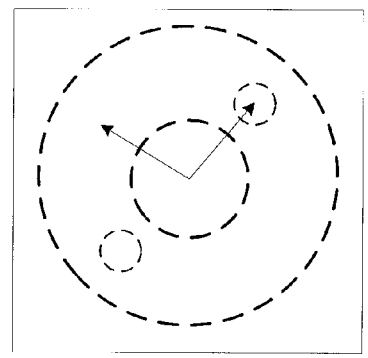

In one preferred embodiment, the cladding region is aligned using a PatMax® model trained synthetically using the circle representing the cladding in the geometric description. In this same embodiment, the stress rods, if present, are each separately aligned using PatMax® models trained using the portions of the geometric model that describe the stress rods. Preferably, this alignment is made more efficient by limiting the search to the area within the aligned cladding circle region. FIG. 4B sketches a typical fiber end-face image and FIG. 4C illustrates the cladding and the stress rods alignment of the fiber end face using synthetic PatMax® models on the image shown in FIG. 4B.

Figure 5A:
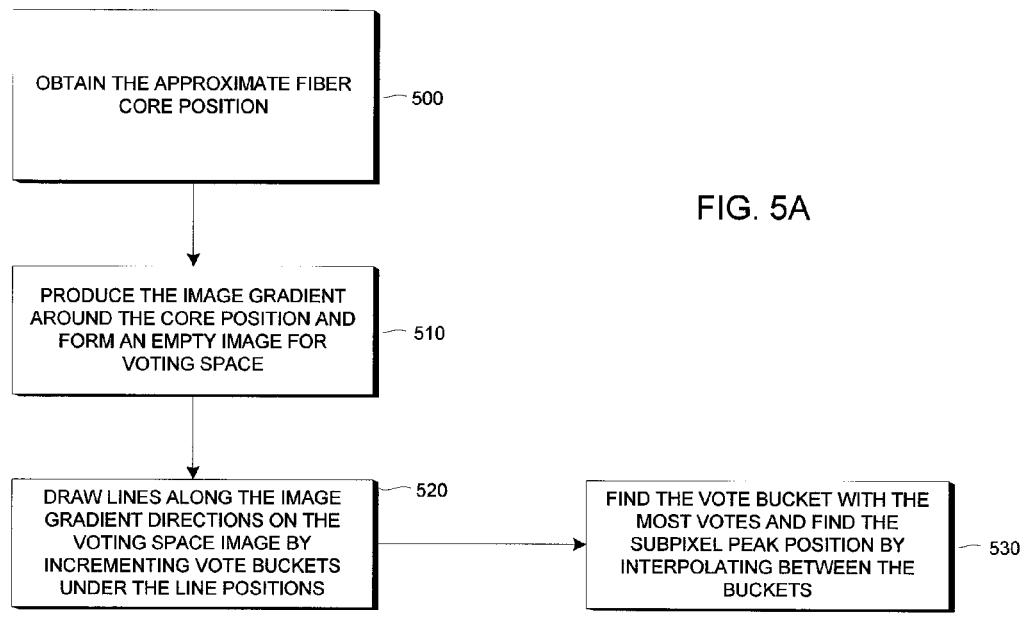
FIG. 5 contains a flowchart 5A and diagrams 5B and 5C for the fiber core localization algorithm.
Figure 5B:
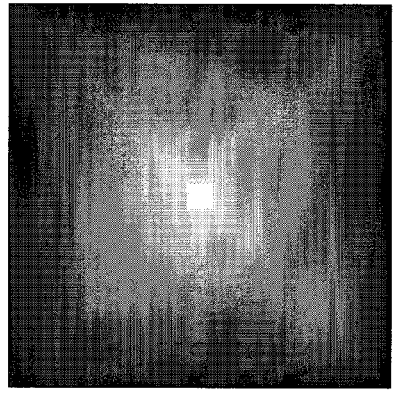
Figure 5C:
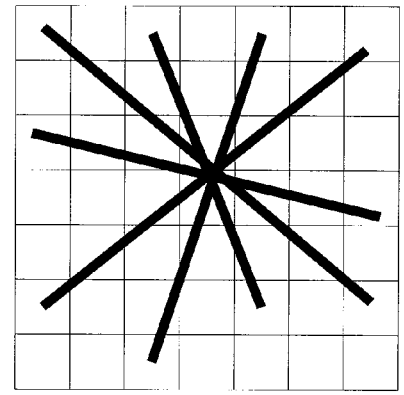

In the same embodiment, the core of the fiber is also aligned in the image as constrained by the center of the aligned cladding region. FIG. 5A shows the flowchart of the method employed to align the fiber core center. In step 500, the approximate position for the fiber core is obtained from the fiber cladding alignment step 310. FIG. 5B shows a typical approximate fiber core enlarged. Next, in step 510, an image gradient is formed for this approximate area. Concurrently, an empty voting space image is formed with a size proportional to the gradient image. The larger the voting space image, the more accurate, but the less efficient, the core alignment method will be. Note that the mapping between the pixels of the approximate core (and gradient) image and the voting space image is defined by corresponding the corners of these images and linearly interpolating between them. The next step 520 entails computing a line along the direction of the gradient angle for each pixel in the gradient image, mapping these lines into the voting space image, and rendering these lines in the voting space image by incrementing the vote counts of the pixels under the lines as shown in FIG. 5C. Finally, the pixel position that has the most votes in the voting image is determined, and the fiber core center position is estimated by interpolating around this position in step 530 and mapping the interpolated position back to the original approximate core image. Note that for core alignment this method is preferred over geometric feature matching methods such as PatMax® because the boundaries of the core region do not typically have high-contrast edges required by feature-matching methods.

Figure 6:
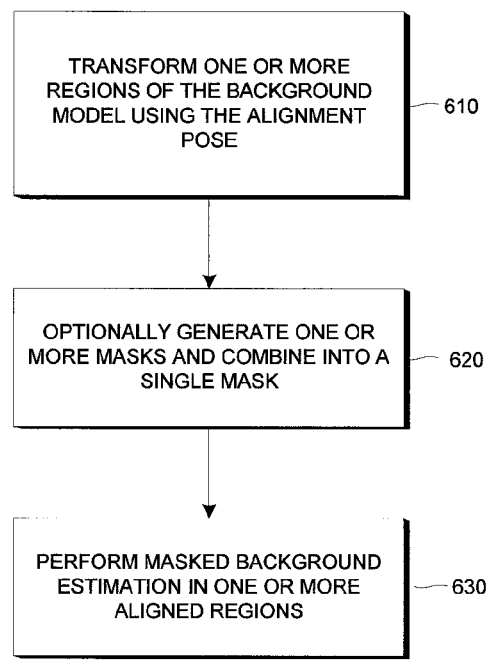
FIG. 6 is a flowchart illustrating steps for background estimation.

FIG. 6 is a flowchart detailing the background estimation 225. Background estimation attempts to estimate the expected non-defective structure from the acquired image using the background model, and it may be performed in one or more of the aligned regions of the model. The regions of the background model are mapped through the alignment pose so that each pixel of the runtime image is assigned to the corresponding region or regions of the model. The techniques for such transformations are known to those skilled in the art.

Background estimation may take as input an optional mask which indicates that only some regions of the image should be used for background estimation. For example, if some parts of the image are known to represent some type of defect already detected by some other technique, or to have some known non-defective structure which would not be properly modelled by the background model, those parts would be indicated as "don't care" in the mask. For example, in fiber end-face inspection, if scratch detection has already been performed, the pixels representing the scratches could be masked out (i.e. marked as don't care).

In some applications, background estimation may also compute an additional mask itself if, for example, some parts of the image seem very likely to be defects even prior to precise background estimation. One technique is to do an initial coarse background estimation using a large filter (e.g. a median filter) to produce a coarse background image, then subtract the coarse background image from the acquired image to produce a coarse foreground image, and then threshold the foreground image with a fairly high threshold to produce a "likely defect mask."

Note that, whatever technique is used to generate the mask, the masked pixels are not marked as defects; they simply do not participate in the background estimation and are thus likely to deviate enough from the background to be marked as defects. Clearly, the mask could alternatively be used to force pixels to be labeled as defect pixels, but this is not the preferred embodiment. The background pixels corresponding to pixels that have been masked out are typically interpolated from the nearest unmasked background pixels in the same region; the type of interpolation may depend on the application. For example, in fiber end-face inspection, if a pixel in the cladding region is masked out, then the background value for that pixel is the background value for the first unmasked background pixel closer to the center of the fiber on a line to the center of the fiber; for the ferrule, a masked pixel uses the radially outward neighbor instead. If there are no such pixels, the values of all nearby unmasked pixels may be used. Alternatively, background pixels may be computed in order by increasing (or decreasing) radius, so that a masked image pixel may effectively be treated as though it were unmasked and had the value of the radially inward (or outward) adjacent pixel in the background image instead of its actual value. These particular interpolation choices are convenient when a smooth radial gradient is expected in the background, but many other choices are possible and within the scope of the present invention.

Using the mask and at least one aligned region, background estimation then proceeds to compute a background value for each pixel in each aligned region of interest, interpolating masked values as necessary. Note that background estimation essentially proceeds independently for each region, so that the pixels of one region are not used in estimating the background for another region, even if the pixels of the two regions are adjacent. This independence can be achieved in a number of ways, the simplest of which is usually to use an additional separate mask for each region, such that the mask for a region has "care" pixels only within that region. The initial mask and any such region mask may be efficiently combined using Boolean or similar operations (e.g., arithmetic minimum or maximum) such that a pixel is a care pixel if and only if it is a care pixel in all the masks being combined.

In many applications, the background will consist of a large-scale (low-frequency) variation, such as that caused by a gradual illumination gradient from one side of the image to the other or by a radial illumination gradient. A low-pass filter is typically a good estimator of such backgrounds, and a preferred embodiment uses a median filter. A nonlinear filter such as a median filter has substantial advantages over linear filters such as a Gaussian or boxcar filter, because linear filters necessarily treat part of the defects as background also, thus degrading sensitivity. By contrast, a median filter will compute the correct background so long as defects occupy less than half of the filter kernel. The optimal size for such a filter depends on the expected sharpness of the gradient and the size of the largest defect that can be detected, and may depend on other factors as well (such as desired execution time). A larger gradient requires a smaller filter to perform an accurate estimate, but larger defects require a larger filter. The proper tradeoff for filter size depends on the particular application. If some of the pixels have been masked out, then the median is computed as the median of the unmasked pixels.

Figure 7:
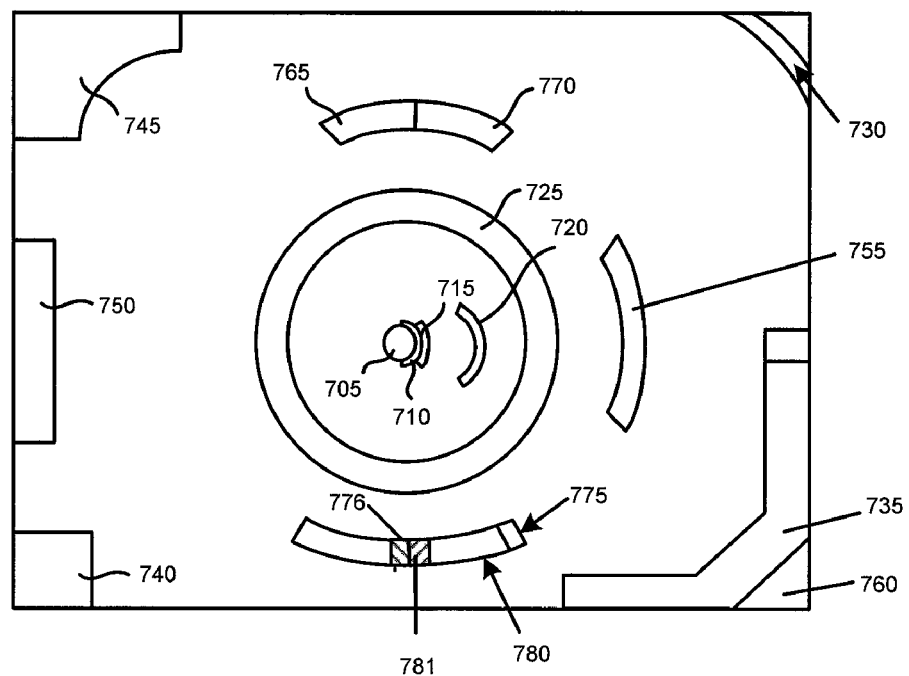
FIG. 7 is a diagram of segments in an annular median filter.

The filter shape may also vary by application. For example, in fiber end-face inspection, a preferred embodiment uses an annular median filter, depicted in FIG. 7. Under typical lighting, the background for a fiber end-face tends to exhibit a radial gradient that is approximately concentric with the fiber cladding. However, there are also non-radial components, e.g. the background intensity halfway to the fiber cladding boundary may be substantially different on the right side of the fiber versus the left, although values nearby on the right at a given radius tend to be similar. To fit this type of variation, the annular median filter splits the image into sections that are circular or elliptical arcs, where the arc angle and the radial extent may vary throughout the image as appropriate. For example, because a very small median size will misinterpret small defects as the background, one should typically set some minimum value for the area of the annular segment, which means that segments near the center will have a larger angular extent and/or a larger radial extent than those near the center of the fiber. For example, segment 705 at the center may actually be a circle instead of an arc, and segment 710 near the center has much greater angular extent that segment 720, which is further out, although the two may (or may not) have similar areas. Segment 715 indicates that one may sometimes use shorter segments near the center in some applications. Segment 725 is an example of a complete circular arc, which may be convenient in cases where there is expected to be only a radial gradient, with no substantial angular variation. It is clear that the edges and the corners of the image warrant somewhat special treatment, since annular segments do not fit well there. Segment 730 represents a straightforward implementation, where the annular segment is simply clipped near the corner. Such a scheme has the disadvantage of producing very small segments near the corners, which thus may be confused by much smaller defects than nearby segment 755 would be. Some alternative shapes for use near edges and corners are shown as segments 735, 740, 745, 750, and 760, although many others are possible. In general, one wants to maintain some minimum size for each segment. For example, when performing fiber end-face inspection in a 640×480 image, where the fiber typically has an apparent diameter of approximately 300 pixels, using a segment size of 81 pixels yields good results. Using an arc length of 81 and a radial extent of 1 for most of the segments (such as 710, 720, and 755) and using center and corner segments shaped such as 705, 735, and 760 is a preferred embodiment. Although segments are depicted as having smooth boundaries, they need to be quantized to the pixel grid, as is known to those skilled in the art.

Also note that segments may be non-overlapping, e.g. segments 765 and 770, or overlapping, e.g. segments 775 and 780. The advantage of overlapping segments is that the median more accurately represents the local neighborhood of a pixel. When using non-overlapping segments, then all background pixels in, e.g., segment 765 are assigned the median of all of those pixels from the image. This technique may sometimes lead to an efficient implementation, since fewer medians need to be computed; however, the background value at pixels such as 766 may be less than optimal because the effective neighborhood is mostly one-sided. By contrast, when using overlapping segments such as 775 and 780, the background value at a given pixel is computed using a segment that is approximately centered on that pixel, and every pixel typically belongs to a unique but overlapping segment. For example, pixel 776 is assigned the median from segment 775, and pixel 781 is assigned the median of segment 780. When using overlapping segments, a "rolling median" is most efficient, since it need only add and remove the pixels that differ between the two segments. Such techniques are known to those skilled in the art.

The choice of an annular median filter for fiber end-face inspection is advantageous not only because the lighting gradients tend to be radial but also because the vast majority of defects (both scratches and spots) are not annular in shape. Thus, a single defect (even one with a fairly large total area) has a fairly small chance of occupying more than half the area of a given annular segment and thus being mistaken for the background. This is another example of the application-specific knowledge that can be applied to the choice of background estimation technique.

Note that the core and the cladding may need to be processed by two separate passes of an appropriately masked annular median filter, because these two components (and thus the expected shading variation) may not be concentric. Typically, the fiber and ferrule can be considered to have the same center for the filter, and making this assumption explicit can improve the efficiency of some implementations. The stress rods, if present, may be processed by an annular median filter centered on the cladding center or on the rod center, or they may be processed by a square median or other type of filter, depending on the expected variation. In cases where the core is found to be concentric with the cladding, use of a single filter may again be possible and more efficient.

There does happen to be one type of defect in fiber end faces that tends to have an annular shape: fretting and epoxy near the cladding/ferrule boundary. This type of defect is particularly problematic for an annular median filter, so a separate technique is used to detect the likely presence of such defects, and then those likely defects are used to contribute to the mask used as an input to the rest of the background estimation, as described above.

An additional advantage of the annular median filter for fiber end-face inspection is that the regions are usually concentric circles (cladding and ferrule, and possibly the core), and thus explicit region masks may not be required because each annular median segment will lie entirely in exactly one region. This is an additional advantage to either using a radial segment extent of 1 or to choosing the annular segment radial boundaries to lie on either side of the region boundaries instead of crossing them.

Figure 8:
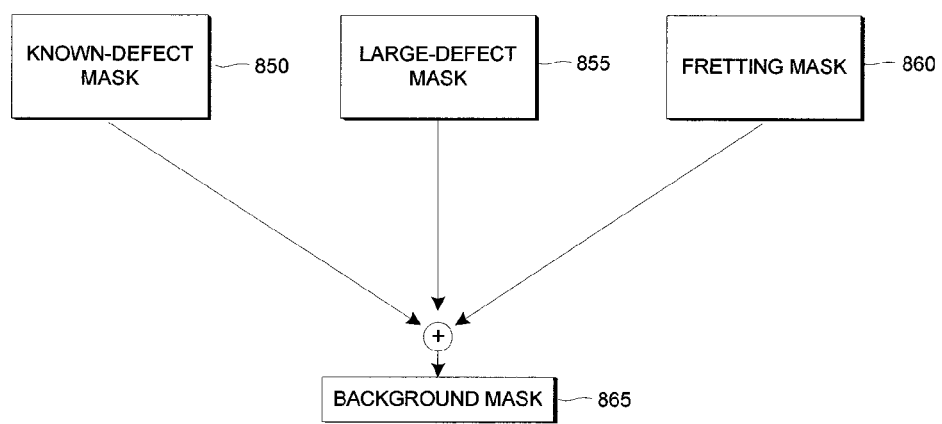
FIG. 8 is a data-flow diagram showing the combination of masks for use in background estimation for fiber end-face inspection.

As mentioned previously, background estimation often makes use of a mask 865, which may be formed from a Boolean or other combination of two or more component masks. For fiber end-face inspection, a preferred embodiment uses three component masks and is illustrated in FIG. 8: a known-defect mask 850 computed prior to background estimation, a large-defect mask 855 computed as part of the background estimation, and a fretting mask 860 computed as part of the background estimation.

The known-defect mask 850 allows the background computation to ignore any areas known a priori to be unrepresentative of the background. Usually the known defects are scratches, and the known-defect mask is called the scratch defect mask. To produce the scratch defect mask, the fiber is subjected to scratch detection, typically using a technique other than the present invention. One technique for detecting scratches is the method for detecting extended defects described in commonly assigned U.S. Pat. No. 6,167,150, entitled "Method and apparatus for detecting extended defects in an object." Any pixel corresponding to part of a scratch is marked as "don't care" in the scratch defect mask.

To produce the large-defect mask 855, an initial coarse background estimation using a very large filter size is performed. A preferred embodiment uses the circumference of the fiber cladding as the annular median filter segment arc length, thus allowing defects up to half the size of the fiber to be detected. The coarse background image is then removed from the image to produce a coarse foreground image, which is then binarized using a fairly high (and typically fixed) threshold to become the large-defect mask. This approach allows defects which are high in contrast, but which are too large to be found by the usual background filter, to be detected. In a typical fiber end-face setup, a value of 20 gray levels for the threshold usually works well.

Figure 11A:
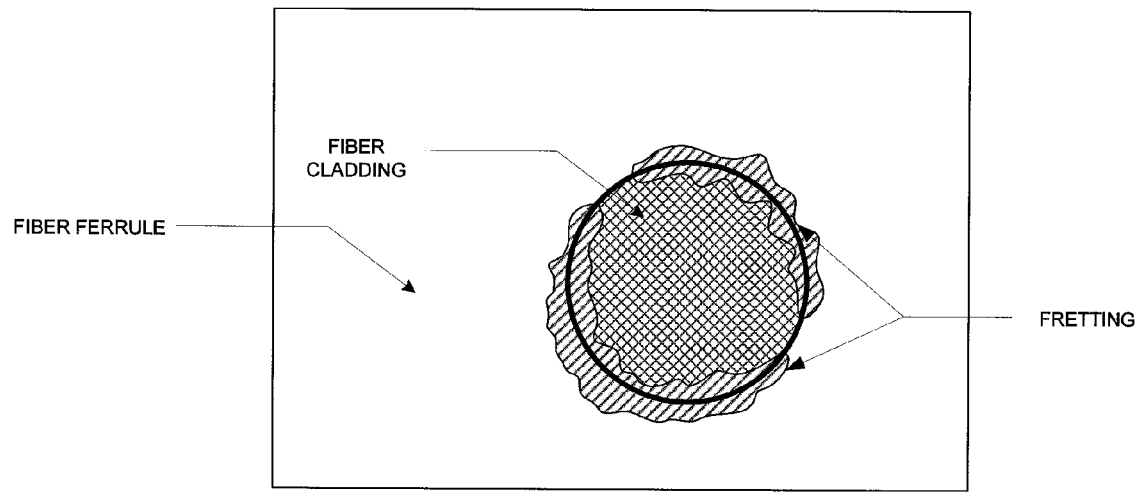
FIG. 11 contains a diagram 11A showing fretting defects and a flowchart 11B illustrating steps for fretting detection.

Fretting is a type of chipping around the fiber cladding and the ferrule border as shown in FIG. 11A. Similarly, the epoxy that bonds the cladding to the ferrule may also appear around the cladding/ferrule border. Both fretting and epoxy usually extend circularly along this border with possible interruptions, and neither should be treated as part of the background. One can avoid mistakenly interpreting epoxy or fretting as background by first detecting regions likely to arise from fretting or epoxy and from these regions forming a fretting mask 860 to use as one component of the background mask 865.

The detection of fretting and epoxy can be done in many ways, all of which are in the scope of the present invention. For example, a low-pass filtering operation will eliminate small structure around the fretting and epoxy and subsequent blob analysis can be used to extract the regions likely to have arisen from fretting and epoxy.

Figure 11B:
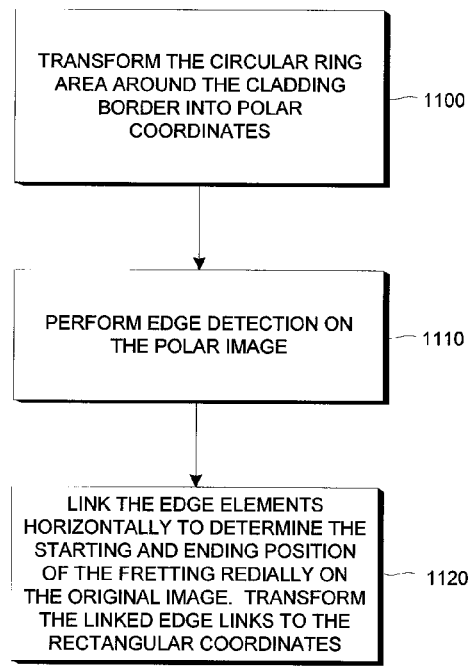

FIG. 11B shows the flow diagram of a preferred embodiment for fretting and epoxy detection. Step 1100 transforms the circular ring around the fiber cladding into polar coordinates such that each row of the polar image is a concentric ring in the original acquired image with a radial extent of one pixel. The alignment pose of the fiber cladding is used to determine the center position for the polar coordinate conversion. Step 1110 applies an edge detection operation to the polar image. Any type of edge detection method that returns edge magnitudes and the peak edge positions can be employed. A preferred embodiment uses Sobel edge detection including "truepeak" (also known as non-maximum suppression). Since each column of the polar image includes the radial extent of the fretting and epoxy, a horizontal edge-linking operation 1120 localizes the inner and the outer ring borders of the fretting and epoxy in the original image. The horizontal edge-linking also makes it possible to skip small gaps reliably. After the linking, the fretting and epoxy borders are transformed back to the rectangular coordinates of the original image to determine the final positions of the fretting and epoxy. The fretting mask is generated by setting each mask pixel that corresponds to fretting to the "don't care" value, and other fretting mask pixels to the "care" value.

Many other background estimation techniques are possible, both in general and for fiber end-face inspection specifically, and all are within the scope of the present invention. For example, a smooth surface may be fitted to each region of the image. The smooth surface could be a polynomial curve and the fitting could use an iterative procedure, with outliers being removed during various iterations, as is known to those skilled in the art. The choice of background estimation technique can be highly application-dependent, but in the absence of application-specific knowledge, a large (e.g. at least 10×10, and possibly much larger) square median filter is often a reasonable choice. A larger square median may be needed to allow for larger defects, while a smaller one may be needed for a rapidly varying background.

Note that the background image may be computed only for some desired aligned regions of the model, or it may be computed for the entire acquired image. It may sometimes be more efficient to compute the background only in desired regions, and sometimes more efficient to compute the background for the entire image, depending on the choice of regions and background estimation technique. The choice is typically made on the basis of computational simplicity and/or execution speed. If the background image is computed even outside the desired regions, the undesired parts are considered invalid and not meaningful, and should not contribute to any results. It may sometimes be useful to use a mask image to represent the valid pixels, as is known to those skilled in the art. If the valid regions are simply rectangles, then one can simply keep track of those valid rectangles and continue to process only within them; this technique can be more efficient than the use of a mask when it is applicable.

In step 230, the background image is removed from the acquired image in one or more of the aligned regions to produce a foreground image in those regions. Again, processing may occur for the entire image or only for those pixels within the desired regions. Removal of the background image typically entails simply subtracting it from the acquired image to produce the foreground image. In a preferred embodiment, the foreground image contains pixels whose values are unsigned (nonnegative), and the subtraction is done so that any results that would have been negative are clamped to zero. In other embodiments, subtraction may be done followed by an absolute value, or even using a foreground image with potentially negative pixel values.

Depending on the background estimation technique, techniques other than subtraction may be more convenient or appropriate. In fact, there may even be cases where the background image need not be explicitly formed in order to remove it from the image, and such cases are within the scope of the present invention; for simplicity, we will still speak of background image computation followed by removal. For example, if the background consists of a particular band of frequencies, then one could remove the background by filtering the image with a band-reject filter for those frequencies, as is known to those skilled in the art. Similarly, the background might consist of some composition of wavelets; such a background also might be able to be removed without being explicitly constructed.

The foreground image contains all the spot defects, which can, in general, be localized by performing blob analysis with suitable threshold values. Depending on the application, a user-specified constant threshold may be feasible. However, for most applications, a constant threshold will not be suitable due to varying defect intensities coupled with the presence of image noise and large intensity variations near the region borders that are not removed by the background estimation and removal processes. There are a number of methods for automatically determining a threshold for a blob analysis, all of which are within the scope of this invention. For example, the P-Tile method uses knowledge about the foreground (in this case, the defects). Alternatively, the mode method employs an image histogram, to which it fits parametric functions in order to model the distribution of background and foreground intensities, then tests the confidence of these fits to in order locate an optimal threshold value at which the histogram can be split into foreground and background. The threshold is computed independently in one or more regions, and different thresholding techniques may be used in each region if desired.

Figure 9:
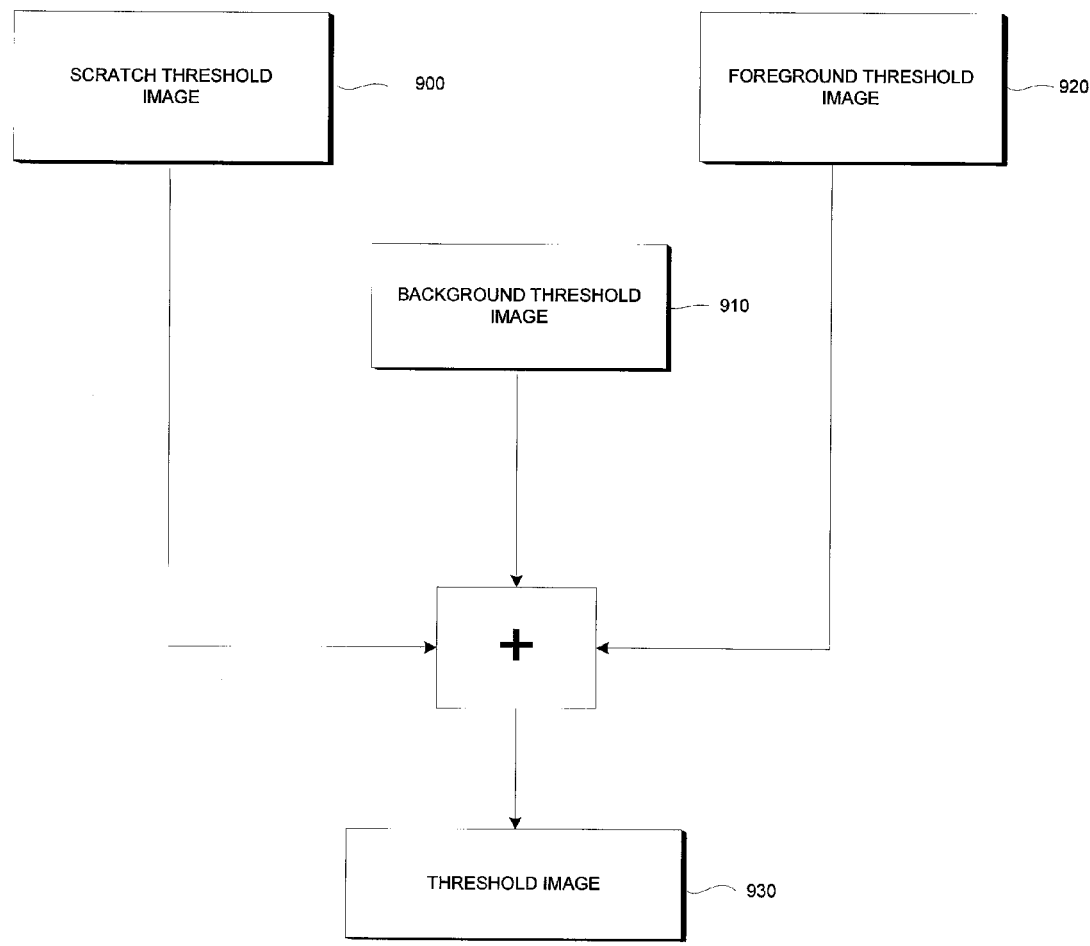
FIG. 9 is a data-flow diagram for automatic defect threshold selection.

In the case of fiber-end inspection, the preferred embodiment applies an automatic thresholding method that makes use of the foreground image and the background image in addition to the region specification, and may also use a separate thresholding mask. FIG. 9 shows the data flow of the automatic thresholding method this invention uses. 900 is a scratch threshold image, wherein pixels found by other techniques to correspond to a scratch have the value of the approximate scratch contrast and non-scratch pixels are set to zero. The scratch threshold image 900 allows spots to be detected on top of scratches only to the extent that the spots differ substantially from the scratch and thus do not appear to be merely part of the scratch. 910 is a background threshold image, computed from the background image using gradient analysis. The background threshold image 910 allows decreased sensitivity to defects, and thus fewer false defects, near areas of rapid variation in the background, e.g. near expected edges. 920 is a foreground threshold image, generated by computing a threshold for each foreground region. The three images 900, 910, and 920 are combined to form threshold image 930, typically by addition, although other techniques are possible and within the scope of the present invention.

Figure 10:
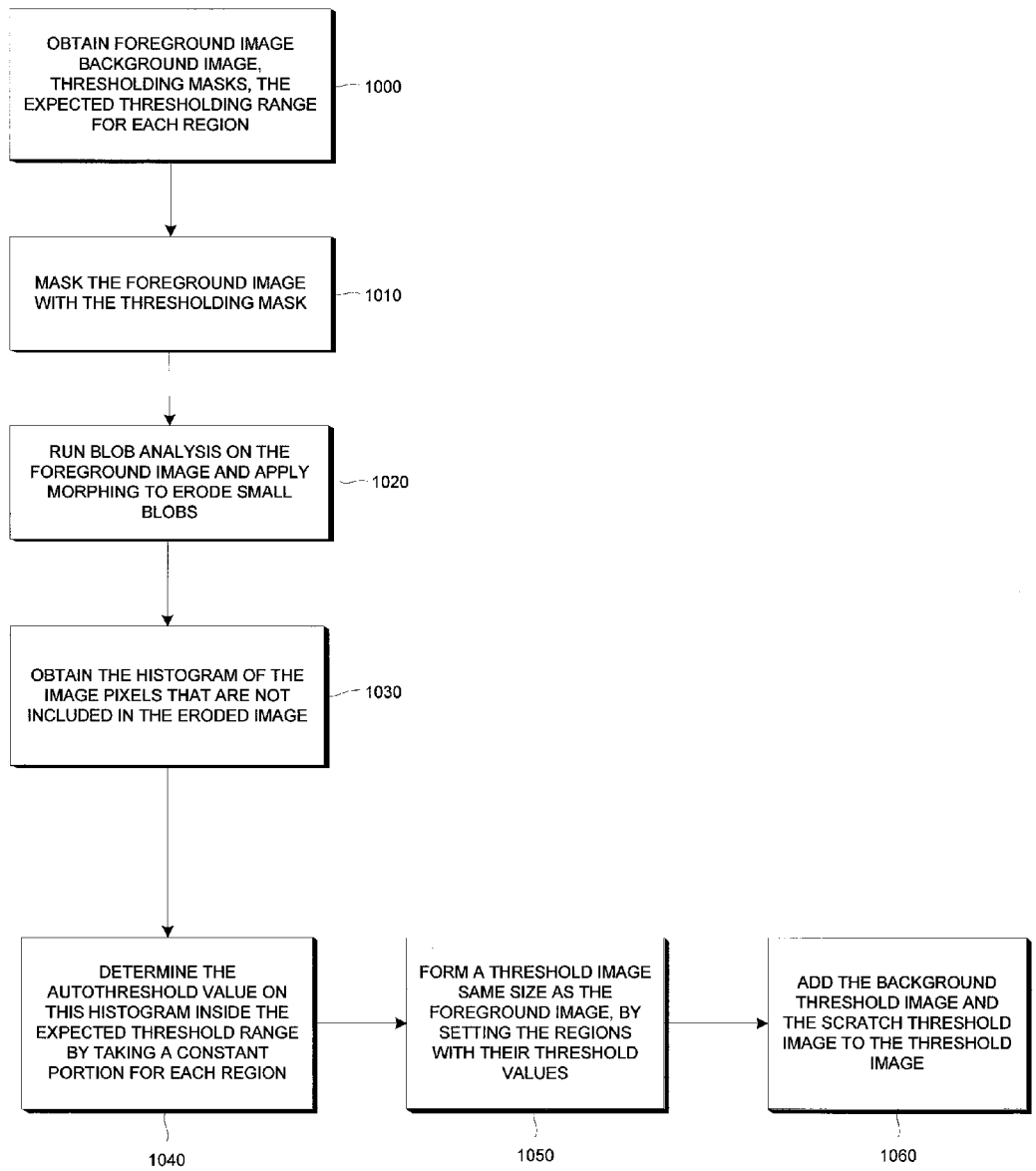
FIG. 10 is a flowchart illustrating steps for threshold selection.

With reference to FIG. 10, in the same embodiment, the foreground image and the background image are obtained in step 1000 from the other stages of the spot detection system, as has already been described. The preferred embodiment accepts an expected threshold range, so that thresholds can be limited by the user; in other words, any result of the automatic thresholding will be clamped to lie within the given range. The threshold range may be specified separately for each region. A thresholding mask which delineates those portions of the images that should have no bearing on threshold detection may also be provided. In the case of fiber end-face inspection, the threshold mask image masks out the regions that correspond to other types of defects such as scratches, cracks, and fretting. In addition the scratch threshold image 900 can also be provided in step 1000.

The step 1010 applies this mask to the foreground image so that only the image areas of interest free of other defect types remain in the image.

The step 1020 binarizes the masked foreground image using the lower end of the expected threshold range for that region as the binarization threshold. The binarization operation will produce an image that contains the spot defects along with noise that appear like small spots. To prevent detecting these small spots as defects, an opening morphology operation is applied to this binary image to generate a new binary image that is used to mark pixels to be ignored in the subsequent histogram calculation 1030. The pixels used in the histogram calculation contain the foreground image noise along with some parts of the valid spots due to the opening operation.

The step 1040 analyzes the part of the histogram of step 1030 between the end points of the expected threshold range. Since this subhistogram includes elements from the valid spots, the preferred embodiment picks a threshold such that a constant percentage of the image elements in this subhistogram have gray levels above the picked threshold. Note that the thresholds are calculated for each geometric region described by the geometric description of the objects to be inspected. The next step 1050, forms a foreground threshold image that has the same size as the foreground image. The thresholds for each geometric region is placed to the corresponding positions to form the foreground threshold image.

In step 1060, the scratch threshold image and background threshold image are added to the foreground threshold image, to form the threshold image 930.

For a number of applications, the border areas between the aligned geometric regions are problematic for blob analysis because the borders may not be correctly detected due to object irregularities, noise, and inaccuracies in the alignment. As a result, it is very difficult to determine a reliable threshold value around these areas. For these kinds of cases the preferred embodiment uses the background image to modify 1060 the threshold image such that the inspection system does not detect any false spots around these problematic areas. In a preferred embodiment, the image gradient magnitude of the background image is calculated and this magnitude image is added to the threshold image. Alternatively, the inverse of the image gradient magnitude might be used to modulate the threshold image (e.g. by image multiplication). This modification to the threshold image increases the thresholds around the places where there are large changes in the background. In other words, the thresholds for the region border areas are increased the most. Note that this modification to the threshold image is not affected by spots with high contrast because such spots are not part of the background image.

After computing the threshold image, at least one aligned region of the foreground image is processed using blob analysis with the threshold image in step 240 to produce candidate defects. Blob analysis using a threshold image is a technique well known in the art; it is equivalent to subtracting the threshold image from the foreground image (clamping values that would be negative to zero) and then performing blob analysis with a constant threshold value of 1. In other words, pixels in the foreground image that exceed the value of the corresponding pixel in the threshold image are considered defect pixels, and the defect pixels are then subjected to connected component analysis to form blobs, which in this context are candidate defects. The classification of pixels as defect or non-defect is referred to as segmentation.

Step 240 may also take as input a defect mask to indicate areas where defects should not be reported. Such a mask can be used by blob analysis, as is known in the art. In the present invention, it is usually most efficient to perform such masking by setting pixels of the threshold image to 255 when the corresponding mask pixel is "don't care."

As is known in the art, it is sometimes useful to use morphology as a preprocessing step after segmentation and prior to performing connectivity analysis. For example, dilation can close small holes and bridge small gaps between unconnected defect pixels and thus sometimes prevent one real defect from breaking up into many small pieces, and erosion can break narrow connections and thus sometimes prevent two nearby real defects from being inadvertently detected as a single defect.

After forming the blobs, it may also be desirable to perform splitting of one blob into multiple defects or merging multiple blobs into a single defect, even beyond that allowed by preprocessing morphology. Such splitting and merging would typically be done using application-specific knowledge of how defects appear. For example, in fiber end-face inspection, it is not uncommon for two nearby spots to be close enough to be detected as a single blob, and it may sometimes be desirable to split such a blob into two defects. Such a case might be detected by examining the blob for a set of gradient edges that would partition the blob into two pieces, or by looking for a narrow neck separating two round subregions. Similarly, a single spot whose average graylevel was close to the threshold might have break up and be detected as two or more separate nearby blobs, and it might be desirable to merge such blobs into a single defect. Such a case might be detected by looking for nearby blobs that all have values near the threshold and, perhaps, that collectively form a reasonable shape.

After forming the candidate defect blobs, it is usually desirable to compute some metrics for them in step 245. Metrics that may be useful include but are not limited to position of the center of mass, angle, area, perimeter, second principal moments of inertia, elongation, and principal-axis-aligned bounding box extents. Techniques for computing such metrics are well known to those skilled in the art, as are techniques for determining the topology of a group of blobs, e.g. which blobs enclose others. For example, defects are often considered significant only if their area exceeds a certain value, or if they occur in a certain location. In fiber end-face inspection, the acceptable area for a defect is usually a function of the distance of the boundary of that defect from the fiber core. Another useful metric may be the the average graylevel of the blob as it appeared in the foreground image (prior to segmentation), which is the average contrast of the defect relative to the local background.

Additionally, one can compute a sub-pixel boundary for a blob; this can be especially useful for more accurately determining the blob's extents, which can be important when only small defects are acceptable. The points of the sub-pixel boundary can also be used to compute a minimum enclosing circle or ellipsoid, as is known to those skilled in the art. Sub-pixel precision can be achieved, for example, by considering the precise boundary to lie at the graylevel threshold, and then interpolating that position using, for example, a linear interpolation between the centers of the boundary pixel and an adjacent outside pixel using the graylevels of those two pixels. Alternatively, edge gradients could be used to compute a subpixel position.

After possibly computing some initial metrics, it may be desirable to classify the candidate defects in step 250 as being either non-defects or defects, or possibly into more than one category of defect. In some applications, this classifcation step may not be necessary, and all candidate defects are trivially classified as defects. The classification may consist, for example, of a set of rules or a neural net, but the use of any classification technique is within the scope of the present invention.

For example, in fiber end-face inspection, candidate defects may be spots, so-called boundary defects, scratches, or too small or faint to be reliably treated as a spot. Scratches and small or faint candidates are both usually treated as non-defects, since scratches are usually detected separately by some other technique. Some example rules for a classifier useful for fiber end-face detection include the following:

1. If a blob is relatively narrow, long, and elongated, then it should be classified as a scratch.
2. If a blob crosses the fiber cladding boundary or is within a few pixels of the cladding boundary, it is a boundary defect.
3. If a blob completely encloses the cladding boundary, it is a boundary defect, specifically a ring of epoxy.
4. If a blob is topologically enclosed by another blob, then it can be ignored (or merged into the enclosing blob), unless the enclosing blob is a ring of epoxy.
5. If subpixel interpolation indicates that the blob is substantially less than even a single pixel wide along one of its principal axes, it should be ignored.

Such rules are meant to be merely illustrative and not restrictive, and a great variety of classification techniques are possible.

Sometimes it is desirable to compute additional metrics after classification of the defects in step 255. For example, in fiber end-face inspection, one might compute a minimum enclosing circle of the subpixel boundary if the candidate defect is a spot, a minimum enclosing circular annulus section (i.e. radial extent and angular extent) if the candidate defect is a boundary defect, and nothing additional if the candidate defect is to be ignored (including scratches). Many other additional metrics are possible, depending on the application.

A software implementation of the above-described embodiment may comprise a series of computer instructions either fixed on a tangible medium, such as a computer readable medium, e.g. a diskette, a CD-ROM, a ROM memory, or a fixed disk, or transmissible to a computer system, via a modem or other interface device over a data communications medium. The medium either can be a tangible medium, including, but not limited to, optical or analog communications lines, or may be implemented with wireless techniques, including but not limited to microwave, infrared or other transmission techniques. It may also be the Internet. The series of computer instructions embodies all or part of the functionality previously described herein with respect to the invention. Those skilled in the art will appreciate that such computer instructions can be written in a number of programming languages for use with many computer architectures or operating systems. Further, such instructions may be stored using any memory technology, present or future, including, but not limited to, semiconductor, magnetic, optical or other memory devices, or transmitted using any communications technology, present or future, including but not limited to optical, infrared, microwave, or other transmission technologies. It is contemplated that such a computer program product may be distributed as removable media with accompanying printed or electronic documentation, e.g., shrink wrapped software, pre-loaded with a computer system, e.g., on system ROM or fixed disk, or distributed from a server or electronic bulletin board over a network, e.g., the Internet or World Wide Web.

Although an exemplary embodiment of the invention has been disclosed, it will be apparent to those skilled in the art that various changes and modifications can be made which will achieve some of the advantages of the invention without departing from the spirit and scope of the invention. For example, although an embodiment for fiber end-face inspection was discussed, those skilled in the art will appreciate that the invention can be applied to a great many other applications, such as inspection of laser diodes or lenses, or inspection of semiconductor wafer pads for probe marks. Use of any such embodiment for the purposes described herein is within the spirit and scope of the invention. Other aspects, such as the specific instructions utilized to achieve a particular function, as well as other modifications to the inventive concept are intended to be covered by the appended claims.

What is claimed is:

1. A method for detecting spot defects in an image of an object, the method comprising:
   acquiring an image of the object at only a single plane of focus;

aligning an alignment model with at least one object region within the image so as to provide at least one aligned object region;

estimating, using the image, a background image representing allowable and expected appearance within the at least one aligned object region, by using a median filter of a larger spatial scale to provide a mask for use with a median filter of a smaller spatial scale;

removing the background image from the image within the at least one aligned object region so as to provide a foreground image having at least one foreground region;

computing a threshold image for at least one of the foreground regions in the foreground image;

applying the threshold image to the foreground image within at least one of the foreground regions so as to provide a defect image; and using connected component analysis to form candidate defects in the defect image.

2. The method of claim 1, further comprising:
classifying candidate defects as one of non-defects, and one of a plurality of possible defect types.

3. The method of claim 1, further comprising:
measuring at least one metric for each candidate defect.

4. The method of claim 3, wherein measuring at least one metric for each defect includes:
measuring sub-pixel boundaries of blobs in the foreground image by edge detection along the boundaries of blobs.

5. The method of claim 3, wherein measuring at least one metric for each defect includes:
measuring sub-pixel boundaries of blobs in the foreground image by tracking along the boundaries of blobs.

6. The method of claim 3, wherein measuring at least one metric for each defect includes:
measuring sub-pixel boundaries of blobs in the foreground image by performing sub-pixel interpolation along the boundaries of blobs.

7. The method of claim 1, wherein aligning performs deformable alignment.

8. The method of claim 7, wherein deformable alignment uses core alignment.

9. The method of claim 1, wherein the object is a fiber-optic end face.

10. The method of claim 1, wherein aligning is performed using a rotation-invariant and scale-invariant alignment method.

11. The method of claim 1, wherein the median filter is an annular median filter.

12. The method of claim 1, wherein the median filter of the larger spatial scale is thresholded to provide the mask.

13. The method of claim 1, wherein estimating includes:
iteratively fitting a smooth surface to the image within the at least one aligned object region.

14. The method of claim 13, wherein the smooth surface is a polynomial curve.

15. The method of claim 13, wherein outliers are removed after each iterative fitting.

16. The method of claim 1, wherein removing includes:
subtracting the background image from the image.

17. The method of claim 1, wherein computing a threshold image for at least one of the foreground regions in the foreground image includes:
removing from the at least one of the foreground regions all pixels with a gray level above a threshold.

18. The method of claim 1, wherein computing a threshold image for at least one of the foreground regions in the foreground image includes:
using histogram analysis.

19. The method of claim 1, wherein computing a threshold image for at least one of the foreground regions in the foreground image includes:
removing, from the at least one of the foreground regions in the foreground image, pixels with a gray level between two prominent peaks of a mufti-modal distribution.

20. The method of claim 1, wherein applying the threshold image to the foreground image within at least one of the foreground regions so as to provide a defect image includes:
subtracting the threshold image from the foreground image within at least one of the foreground regions so as to provide a defect image.

21. A method for detecting spot defects in an image of an object, the method comprising:
acquiring an image of the object at only a single plane of focus;

aligning an alignment model with at least one object region within the image so as to provide at least one aligned object region;

estimating, using the image, a background image representing allowable and expected appearance within the at least one aligned object region;

removing the background image from the image within the at least one aligned object region so as to provide a foreground image having at least one foreground region;

computing a threshold image for at least one of the foreground regions in the foreground image by adding the gradient of the background image to the threshold image;

applying the threshold image to the foreground image within at least one of the foreground regions so as to provide a defect image; and using connected component analysis to form candidate defects in the defect image.

* * * * *